United States Patent
Oneda et al.

(10) Patent No.: US 6,174,280 B1
(45) Date of Patent: Jan. 16, 2001

(54) SHEATH FOR PROTECTING AND ALTERING THE BENDING CHARACTERISTICS OF A FLEXIBLE ENDOSCOPE

(75) Inventors: Katsumi Oneda, Alpine, NJ (US); E. Paul Harhen, Duxbury, MA (US); Isao Fujimoto, Cresskill, NJ (US)

(73) Assignee: Vision Sciences, Inc., Natick, MA (US)

( * ) Notice: Under 35 U.S.C. 154(b), the term of this patent shall be extended for 0 days.

(21) Appl. No.: 09/196,570

(22) Filed: Nov. 19, 1998

(51) Int. Cl.[7] ....................................................... A61B 1/00
(52) U.S. Cl. .................................................. 600/121; 600/114
(58) Field of Search ................................... 600/114, 121, 600/123, 136, 138, 143, 144; 604/281, 282

(56) References Cited

U.S. PATENT DOCUMENTS

| | | | |
|---|---|---|---|
| 4,577,621 | * 3/1986 | Patel | 600/114 |
| 4,646,722 | * 3/1987 | Siverstein et al. | 600/104 |
| 4,800,870 | * 1/1989 | Reid, Jr. | 600/104 |
| 4,815,450 | * 3/1989 | Patel | 600/115 |
| 4,890,602 | * 1/1990 | Hake | 600/144 |
| 4,971,033 | * 11/1990 | Ehlers | 600/139 |
| 4,977,887 | * 12/1990 | Gouda | 600/144 |
| 5,025,778 | * 6/1991 | Silverstein et al. | 600/104 |
| 5,197,457 | * 3/1993 | Adair | 600/104 |
| 5,199,417 | * 4/1993 | Muller et al. | 600/128 |
| 5,217,001 | * 6/1993 | Nakao et al. | 600/123 |
| 5,483,951 | * 1/1996 | Frassica et al. | 600/104 |
| 5,607,386 | * 3/1997 | Flam | 600/120 |
| 5,702,347 | * 12/1997 | Yabe et al. | 600/121 |
| 5,733,242 | * 3/1998 | Rayburn et al. | 600/120 |
| 5,885,209 | * 3/1999 | Green | 600/153 |

\* cited by examiner

*Primary Examiner*—John P. Leubecker
(74) *Attorney, Agent, or Firm*—Dorsey & Whitney LLP

(57) ABSTRACT

A sheath for use with an endoscope having a flexible insertion tube to isolate at least a portion of the insertion tube from an external environment, and to alter the bending characteristics of at least a portion of the insertion tube, is shown and described. The sheath includes a compliant tube and an elongated shape-retaining member attached to the compliant tube. The compliant tube has a proximal end having an interior area configured to receive a first portion of the flexible insertion tube. The shape-retaining member extends axially along a second portion of the flexible insertion tube when the first portion of the flexible insertion tube is positioned in the interior area of the compliant tube. The shape-retaining member is sufficiently stiff to remain in a selected shape or position, and to retain the second portion of the flexible insertion tube in the selected shape or position. The shape-retaining member in one embodiment is rigid, and in another embodiment is sufficiently bendable to allow the operator to conform the insertion tube to other selected shapes or positions. In another alternate embodiment, the sheath has a rigid, shape-retaining member along a first portion of the sheath, a bendable shape-retaining member along a second portion of the sheath, and the compliant tube along a distal portion of the sheath.

26 Claims, 6 Drawing Sheets

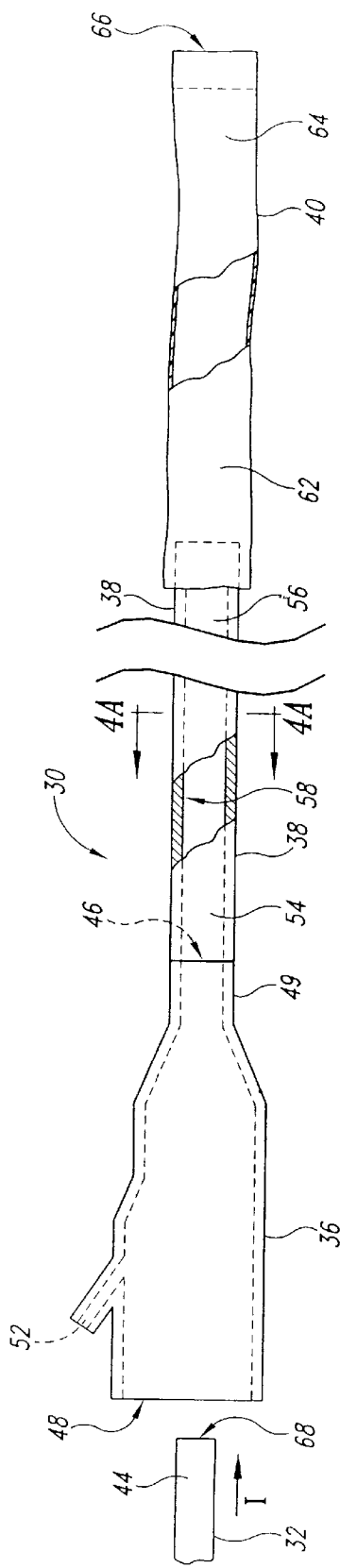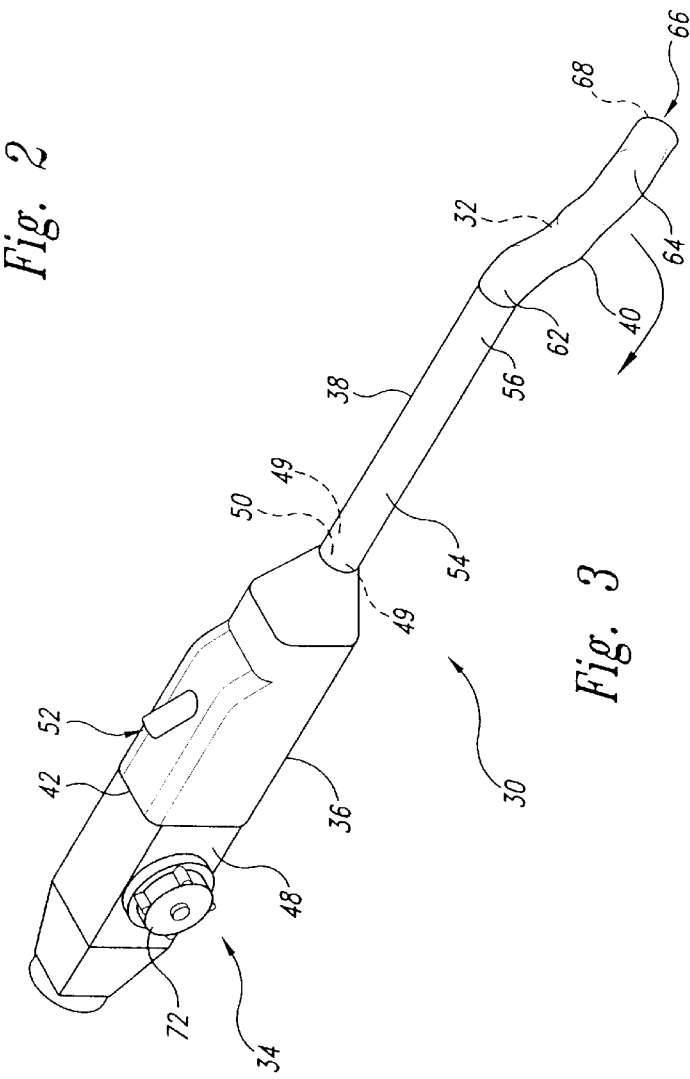
Fig. 2
Fig. 3

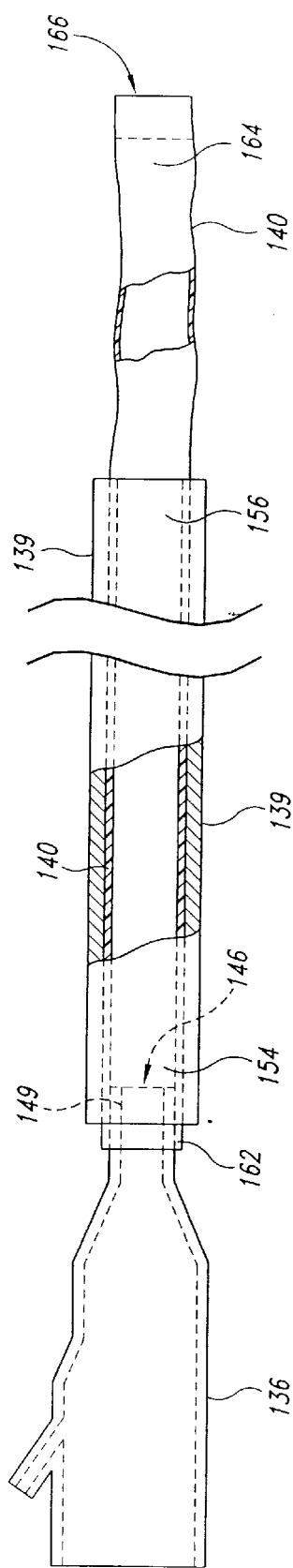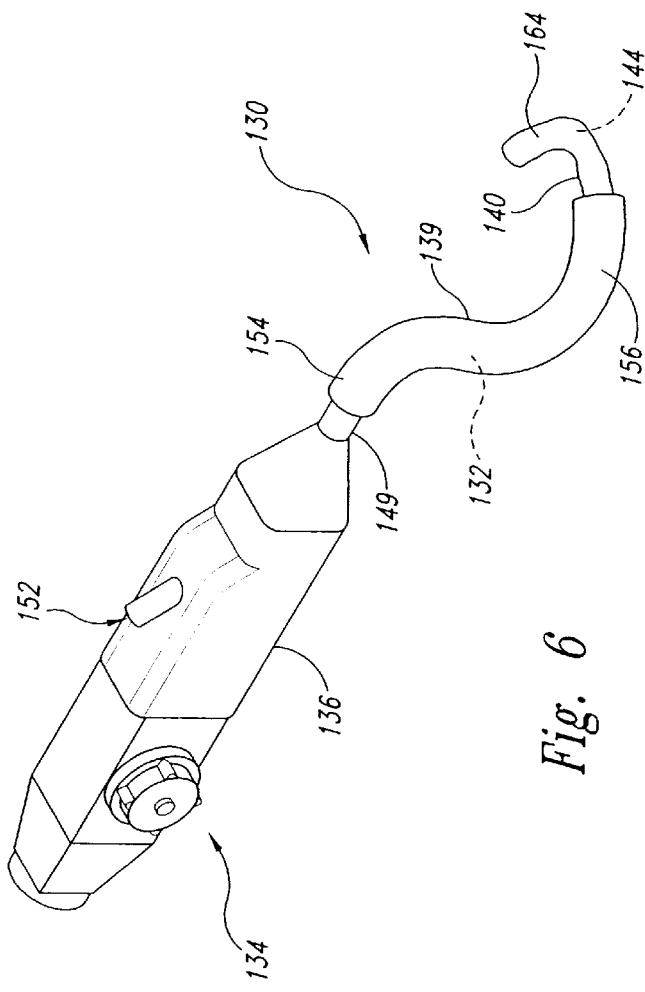
Fig. 5
Fig. 6

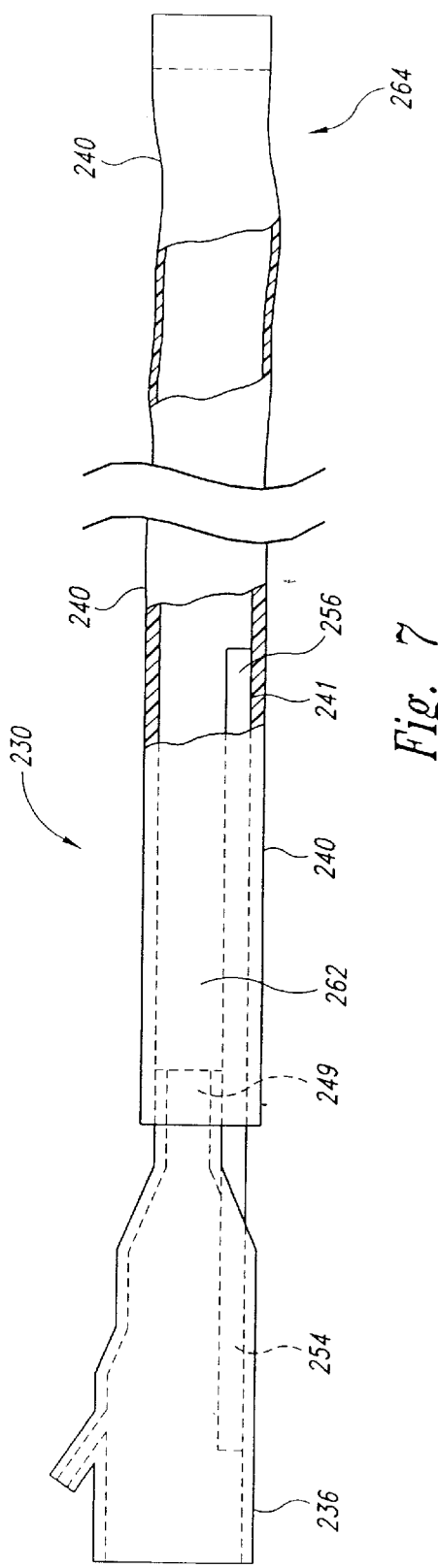
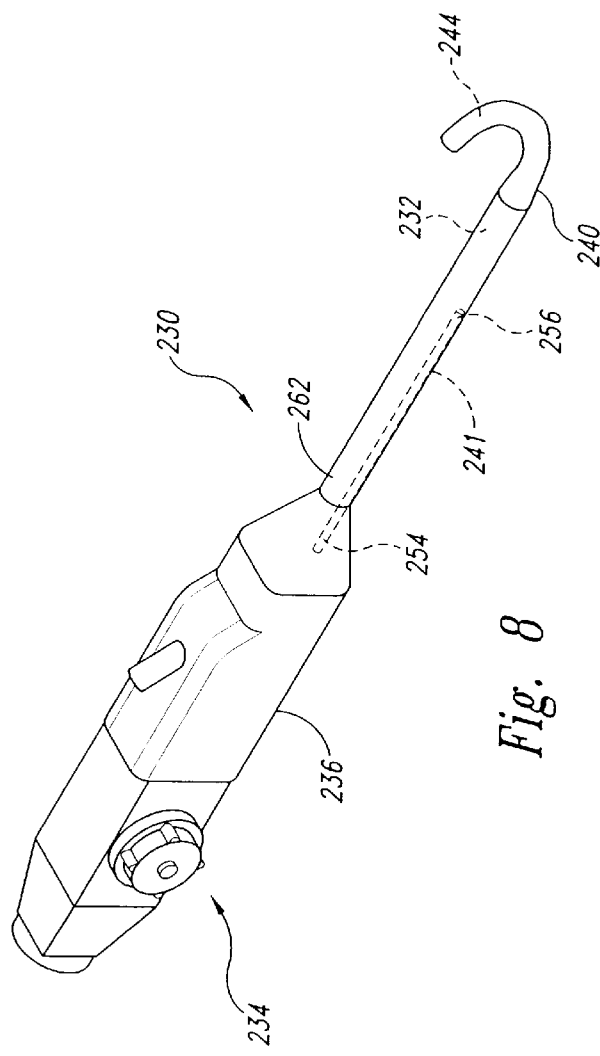
Fig. 7
Fig. 8

SHEATH FOR PROTECTING AND ALTERING THE BENDING CHARACTERISTICS OF A FLEXIBLE ENDOSCOPE

TECHNICAL FIELD

The invention relates to surgical, therapeutic and diagnostic equipment. More particularly, the invention relates to endoscopes, flexible endoscopic insertion tubes and sheaths for isolating the insertion tubes from an external environment.

BACKGROUND OF THE INVENTION

The use of intrabody medical equipment, such as endoscopes, catheters, and the like, for surgical, diagnostic and therapeutic purposes is rapidly expanding. To improve performance, the equipment has been optimized to best accomplish selected purposes. For example, endoscopes have been optimized and refined to provide upper endoscopes for examination of the esophagus, stomach, and duodenum; colonoscopes for the colon; angioscopes for blood vessels; bronchoscopes for the bronchi; laparoscopes for the peritoneal cavity; arthroscopes for joint spaces; nasopharygoscopes for nasal passages and the pharynx; and intubation scopes for a person's airway.

A conventional endoscope 11, shown in FIG. 1, has an insertion tube 12 that is connected at a proximal end 14 to a handle or headpiece 16. The insertion tube 12 is adapted to be inserted into a patient's body to perform a selected surgical, therapeutic or diagnostic procedure. The endoscope 11 is generally manufactured with either a rigid or flexible insertion tube 12. The rigid insertion tube 12 maintains its shape to allow the operator to change the position of the portion of the insertion tube 12 that is within the body by applying torque to the portion of the endoscope 11 that is outside the body. The flexible insertion tube 12, on the other hand, cannot be controlled in such a manner. Instead, control wheels 24 are mounted on the headpiece 16 and connected to the insertion tube's distal end 20 by control cables (not shown). The control wheels 24 are manipulated to bend the insertion tube's distal end 20 to move the distal end 20 up, down, left, or right. Accordingly, the distal end 20 can be controlled to allow improved visibility or positioning of working tools within the patient's body.

The insertion tube 12 often contains an imaging system 18 having optical fibers or the like extending along the length of the insertion tube and terminating at a viewing window 19 in the insertion tube's distal end 20. The imaging system 18 conveys an image from a viewing window 19 to an eyepiece 22 on the headpiece 16, or to a monitor (not shown), so that the user can see into a selected body cavity during an endoscopic procedure. Through manipulation of the control wheels 24, an operator can cause the distal end 20 of the insertion tube 12 to become substantially linear, or to take a curved shape (two possible curves being illustrated in FIG. 1) to selectively position the viewing window 19. The endoscope 11 is described in greater detail in U.S. Pat. No. Re 34,110 and U.S. Pat. No. 4,646,722, which are incorporated by reference.

Different endoscopic procedures are best performed with endoscopes having insertion tubes with particular bending characteristics. For example, laparoscopy is typically performed with an endoscope having a rigid or semi-rigid insertion tube. Endoscopic intubation is also performed with a rigid endoscope so as to allow for positioning with leverage during insertion into the body. Other endoscopic procedures use endoscopes with flexible insertion tubes, such as colonoscopes, bronchoscopes and arthroscopes. Thus, facilities need several different endoscopes. The endoscopes, however, are not suitably interchangeable between procedures. Endoscopes can be expensive and, as a result, owning large numbers of them is often cost prohibitive.

While endoscopes provide an excellent way to perform selected, minimally invasive surgeries in a time and cost effective manner, some endoscopes have limited versatility for performing a range of endoscopic procedures. Endoscopes with rigid insertion tubes have limited versatility because the insertion tube's distal end cannot be steered around corners. Accordingly, the rigid endoscopes may not be able to access or view particular areas in a body cavity. In certain of these situations, endoscopes with flexible or semi-rigid insertion tubes could work well. Flexible insertion tubes, however, have other limitations which are described below.

Rigid endoscopes are typically made from metal, such as stainless steel, and therefore could be sterilized in an autoclave prior to surgery. Endoscopes having flexible insertion tubes, on the other hand, typically have a flexible outer coating, such as a rubberized material, and, as a result, could not be safely autoclaved. As a result, flexible endoscopes are usually more difficult to thoroughly sterilize. Thus, for sterility reasons, minimally invasive surgery was traditionally performed most often with endoscopes having rigid insertion tubes.

To solve some of these problems, protective endoscopic sheaths have been developed to protect insertion tubes from the contaminated external environment, and to protect patients from contaminated insertion tubes. U.S. Pat. No. 4,646,722 to Silverstein et al., for example, shows a flexible sheath for surrounding the flexible insertion tube of the endoscope. A protective, flexible sheath that is both sterile and disposable can be placed over either a rigid or flexible insertion tube to prevent the insertion tube from being contaminated. After use, the sheath can be discarded. The endoscope can be prepared for the next procedure by merely replacing the sheath with a new, sterile sheath, thereby considerably reducing preparation and down time of the endoscope between procedures.

There is a need for an endoscope system that achieves the benefits of an endoscope with rigid insertion tubes as well as the benefits of an endoscope with a flexible insertion tube. There is also a need for an endoscope system that overcomes the limited versatility of endoscopes having rigid insertion tubes and the sterilization difficulties experienced by endoscopes having flexible insertion tubes. Accordingly, there is a need for an endoscope system that allows one endoscope to be used effectively and efficiently for a range of procedures which typically require insertion tubes with different bending characteristics.

SUMMARY OF THE INVENTION

The present invention provides a sheath for flexible endoscopic insertion tubes that overcomes problems experienced in the prior art. In an exemplary embodiment, the sheath is configured to isolate at least a portion of an insertion tube from an external environment, and to alter the bending characteristics of the insertion tube. Embodiments of the sheath give at least a portion of a flexible insertion tube the bending characteristics of a rigid or semi-rigid insertion tube.

In one embodiment, the sheath includes an elongated, compliant tube and an elongated, shape-retaining member attached to the compliant tube. The compliant tube has a proximal end with an opening configured to receive the flexible insertion tube during installation. The compliant tube isolates at least a portion of the flexible insertion tube from the external environment.

The shape-retaining member is positioned to extend axially along a portion of the flexible insertion tube when the insertion tube is in the compliant tube. The shape-retaining member has a sufficient stiffness to maintain a selected shape and to retain the portion of the flexible insertion tube in the selected shape.

In an other embodiment of the present invention, the shape-retaining member is shapeable to allow the user to adjust its shape. The shapeable member of this embodiment is bendable to the selected shape, and has a stiffness sufficient to maintain the selected shape and to retain the portion of the flexible insertion tube in the selected shape. The stiffness is also sufficient to prevent the portion of the flexible insertion tube from moving the shape-retaining member away from the selected shape.

In yet another embodiment of the present invention, the shape-retaining member is rigid and substantially non-shapeable. The rigid shape-retaining member securely retains the portion of the flexible insertion tube in the selected shape when the flexible insertion tube is positioned in the compliant tube.

BRIEF DESCRIPTION OF THE DRAWINGS

FIG. 2 is a two-part, partially cut-away, side elevation view of a partially rigid sheath according to one embodiment of the present invention and a portion of an endoscopic insertion tube shown prior to insertion into the sheath.

FIG. 3 is a reduced isometric view of the sheath of FIG. 2 installed on the insertion tube.

FIG. 5 is a two-part, partially cut-away, side elevation view of a partially shapeable sheath according to an alternate embodiment of the present invention.

FIG. 6 is a reduced isometric view of the sheath of FIG. 5 installed on a flexible insertion tube of an endoscope.

FIG. 7 is a two-part, partially cut-away, side elevation view of a sheath according to another alternate embodiment of the present invention.

FIG. 8 is a reduced isometric view of the sheath of FIG. 7 installed on a flexible insertion tube of an endoscope.

DETAILED DESCRIPTION OF THE INVENTION

Figure 1:
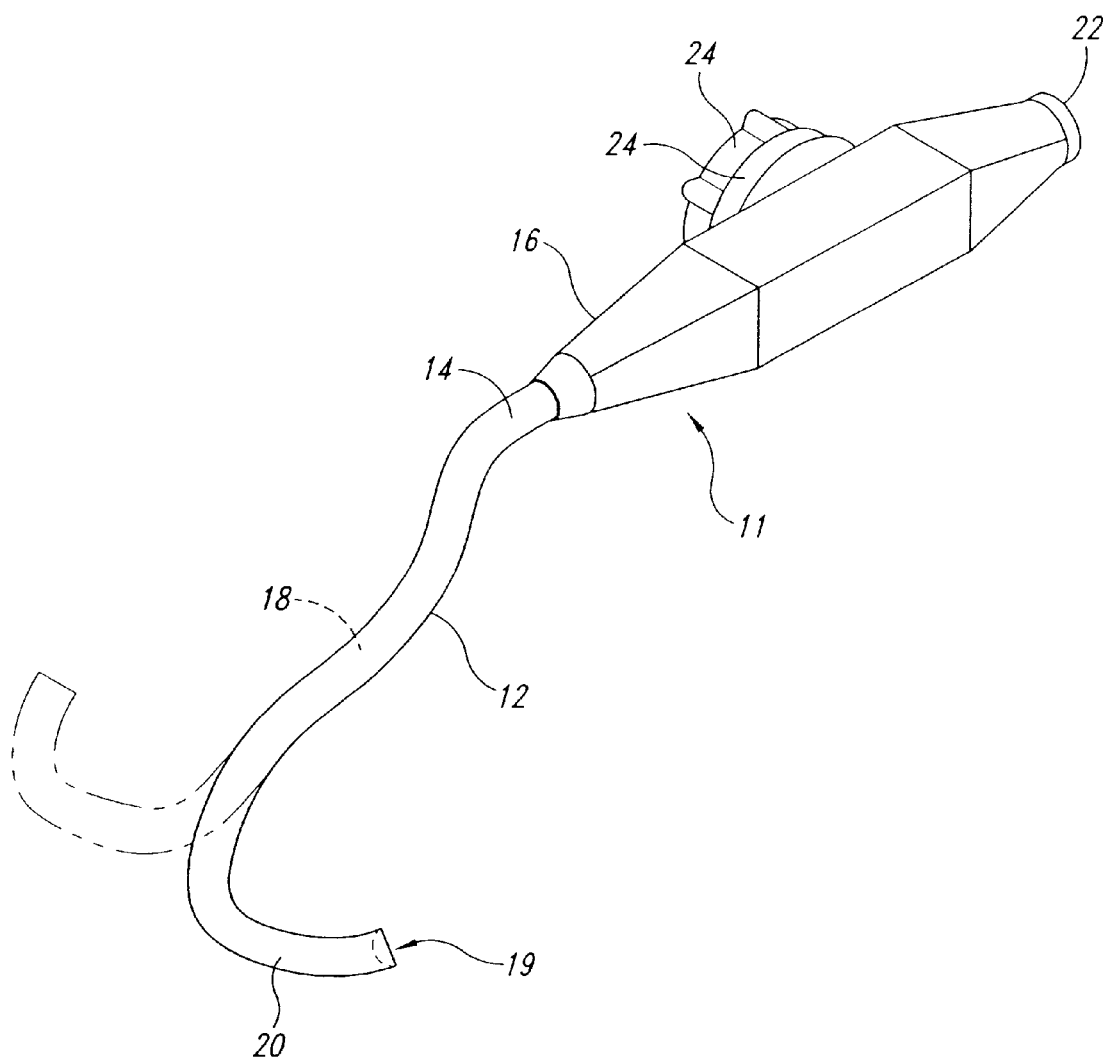
FIG. 1 is an isometric view of a prior art endoscope with a flexible insertion tube.

The present invention is generally directed toward a sheath for isolating an endoscopic insertion tube from an external environment, and for altering the bending characteristics of the flexible insertion tube. Several embodiments of the sheath alter the bending characteristics from that of a flexible insertion tube to one that is rigid or semi-rigid, or shapeable. The sheath also isolates the flexible insertion tube from a contaminated environment during an endoscopic procedure. As a result, endoscopes having flexible insertion tubes can be used in situations traditionally requiring endoscopes having rigid or semi-rigid insertion tubes. The flexible insertion tubes also do not need to be sterilized between uses because a sterile sheath is installed for each procedure. Many specific details of certain embodiments of the invention are set forth in the following description and shown in FIGS. 2–10 to provide a thorough understanding of such embodiments. One skilled in the art, however, will understand that the present invention may have additional embodiments, or that the invention may be practiced without several of the details described in the following description.

By shapeable, it is intended to mean that the element is sufficiently pliable to be deformed by hand, but sufficiently stiff to retain a given shape once released. In addition, the shapeable element is sufficiently stiff to maintain its shape against any restoring force exerted by the flexible insertion tube contained within the shapeable element. In contrast, a rigid insertion tube is rigid along its entire length, and is too stiff to be effectively bent.

FIGS. 2 and 3 show one embodiment of an endoscopic sheath 30 for isolating a flexible insertion tube 32 of an endoscope 34 (FIG. 3) from an external environment. In the illustrated embodiment, the sheath 30, while in place, gives the flexible insertion tube 32 the bending characteristics of a semi-rigid insertion tube, i.e., one that is rigid along a portion of its length. The sheath 30 includes a body 36, a shape-retaining member 38 attached at a proximal end 54 to the body 36, and a compliant tube 40 receiving a distal end 56 of the shape-retaining member 38.

The body 36 has a proximal opening 42 and a distal opening 46 for receiving the insertion tube 32 therethrough during installation of the sheath 30 on the endoscope 34. The proximal opening 42 is configured to closely receive a portion of the headpiece 48 (FIG. 3) of the endoscope 34 when the insertion tube 32 is fully inserted into the sheath 30. The distal opening 46 of the body 36 is reduced at a neck 49 to closely retain a proximal end 50 (FIG. 3) of the insertion tube 32 in a fixed alignment. The body 36 can also have a working port 52 for receiving an elongated, endoscopic accessory, such as a biopsy device (not shown), for use during a selected endoscopic procedure. In the illustrated embodiment, the body 36 is fabricated from injection-molded, rigid plastic. The body 36 can be fabricated from any other suitable material, and, depending on the specific material used, can be manufactured through other processes.

As best seen in FIG. 2, the shape-retaining member 38 is an elongated, hollow member having an interior wall 58 that defines an interior area sized to slidably receive at least a portion of the insertion tube 32. In the illustrated embodiment, an inner diameter of the interior wall 58 of the sheath 30 is slightly larger than an external diameter of the insertion tube 32 to allow the insertion tube 32 to be easily inserted into the sheath 30.

The shape-retaining member 38 is rigid, i.e., substantially "non-bendable" upon application of forces typically experienced during an endoscopic procedure. Accordingly, the shape-retaining member remains in the selected shape during the endoscopic procedure. The shape-retaining member 38 also retains the portion of the flexible insertion tube 32 within it in the selected shape and substantially prevents that portion of the flexible insertion tube 32 from moving out of the selected shape while the sheath 30 is installed on the endoscope 34. The shape-retaining member 38 is sealably connected to the sheath's body 36 and is impermeable so it isolates the enclosed portion of the insertion tube 32 from the external environment. In the illustrated embodiment, the shape-retaining member 38 is fabricated from a length of rigid plastic tubing. The shape-retaining member 38 could also be fabricated from a metal tube, or from another suitable material or structure to provide a rigid proximal section of the sheath 30. The length of the shape-retaining member 38, and the portion of the insertion tube 32 retained by the shape-retaining member 38, can be varied between sheaths to accommodate the needs of selected endoscopic procedures.

As illustrated in FIGS. 2 and 3, the proximal end 54 of the shape-retaining member 38 is butted against the neck 49 around the distal opening 46 of the body 36, but it can be attached in other suitable configurations. A central axis of the distal opening 46 is collinear with a central axis of the proximal end 54 of the shape-retaining member 38.

Figure 4A:
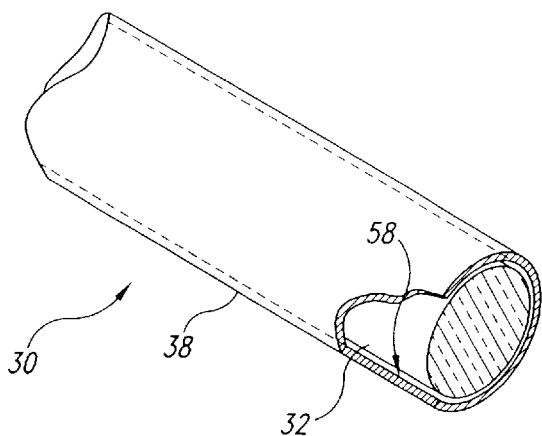
FIG. 4a is an enlarged, partially cut-away isometric view of a central portion of the sheath of FIG. 2 covering a central portion of the insertion tube.
Figure 4B:
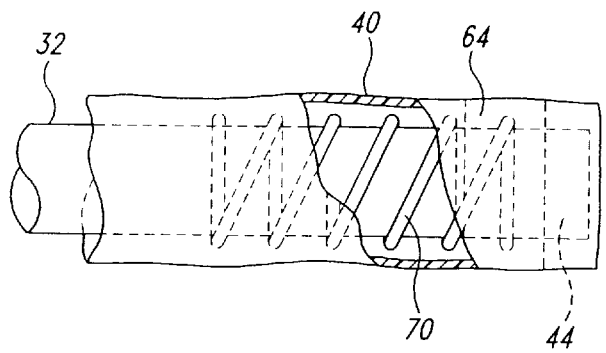
FIG. 4b is an enlarged, partially cut-away, side elevation view of a distal portion of the sheath of FIG. 2 covering a distal portion of the insertion tube.

The sheath's compliant tube 40 is a flexible elastomeric tube having a proximal end 62 connected to the shape-retaining member 38 and a distal end 64 opposite the proximal end. The compliant tube 40 is sized to receive a distal end 44 of the insertion tube 32 so that the sheath's distal end 64 is immediately adjacent to the insertion tube's distal end 44. In the illustrated embodiment, the proximal end 62 of the compliant tube 40 overlaps and is adhered to the distal end 56 of the shape-retaining member 38. The compliant tube 40 can overlap some or all of the shape-retaining member 38, and can be cemented, glued, or affixed by other suitable means. The distal end 64 of the compliant tube 40 is sealed to isolate the insertion tube 32 from the external environment. As best illustrated in FIG. 4b, an inner diameter of the compliant tube 40 is slightly larger than the outer diameter of the insertion tube 32 to allow the insertion tube 32 to be easily inserted into the sheath 30.

In the exemplary embodiment, a sheath window 66 at the extreme distal end 64 of the compliant tube 40 is positioned to correspond to a complementary viewing window 68 on the extreme distal end 44 of the insertion tube 32. The sheath window 66 is preferably clear, however, it can be shaded or tinted to meet varying needs. As illustrated in FIG. 4b, a helical coil 70 can be inserted inside the distal end 64 of the compliant tube 40 to encircle the distal end 44 of the insertion tube 32 and retain the insertion tube in alignment with the distal tip 64 of the compliant tube 40. Alternate embodiments use other techniques to hold the insertion tube's distal end 44 immediately adjacent the sheath's distal end 64. As an example, a locking mechanism (not shown) on the sheath's distal end 64 can positively engage the insertion tube's distal end 44 to releasably hold the insertion tube 32. In another alternate embodiment, the sheath's length is shorter than the insertion tube's length, so the compliant tube 40 is stretched axially when the sheath 30 is installed. The axial tension holds the sheath window 66 immediately adjacent the insertion tube's viewing window 68.

Figure 4C:
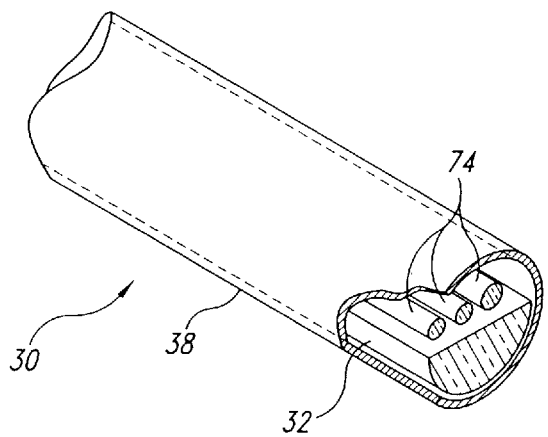
FIG. 4c is an enlarged, partially cut-away isometric view of a central portion of a sheath covering a central portion of an endoscopic insertion tube according to an alternate embodiment of the present invention.

In one embodiment, illustrated in FIG. 4c, the sheath has a substantially circular cross-sectional shape, and the insertion tube 32 has a different cross-sectional shape, such as a D-shape. The D-shaped insertion tube 32 is sized to fit in approximately half of the sheath, so sufficient space is provided adjacent to the insertion tube 32 within the interior area for endoscopic channels 74, such as an air channel, a water channel, and a working or suction channel. These channels 74 are sealably connected to openings in the sheath's distal end 64 to allow air, water and an endoscopic accessory to pass through the sheath's distal end 64, while the insertion tube 32 remains isolated from the contaminated environment.

Figure 4D:
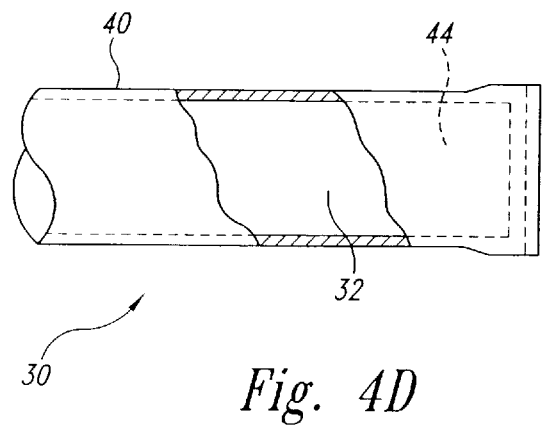
FIG. 4d is an enlarged, partially cut-away, side elevation view of a distal portion of a sheath covering a distal portion of an endoscopic insertion tube according to an alternate embodiment of the present invention.

In another alternate embodiment, illustrated in FIG. 4d, the inner diameter of the compliant tube 40 is slightly smaller than the outer diameter of the insertion tube 32. In this embodiment, the sheath 30 is retained in the proper position on the insertion tube 32 at least in part by the radial compression generated by the restoring force of the compliant tube 40 caused by the compliant tube being stretched around the insertion tube.

In operation, the flexible insertion tube 32 of the endoscope 34 is inserted into the sheath 30 so the insertion tube is isolated from the external environment. As best seen in FIG. 2, the distal end 44 of the insertion tube 32 is first aligned axially with the proximal opening 42 in the body 36. The insertion tube 32 is moved axially into the sheath 30 in the direction I with the insertion tube extending through the sheath's body until the distal end 44 of the insertion tube 32 contacts the distal end 64 of the compliant tube 40. In the illustrated embodiment, the headpiece 48 contacts the proximal opening 42 of the body 36 and the distal end 44 of the insertion tube 32 contacts the distal end 64 of the compliant tube 40 simultaneously. A portion of the flexible insertion tube 32 is positioned within the shape-retaining member 38 so that portion of the insertion tube conforms to the shape of the shape-retaining member 38. The rigid shape-retaining member 38 has a sufficient stiffness to retain the corresponding portion of the insertion tube 32 in the selected shape during the endoscopic procedure.

The sheath 30 and insertion tube 32 are then inserted as a unit into an opening or orifice in a patient until the distal end 44 of the insertion tube 32 is near the point where the procedure will occur. As the insertion tube 32 and sheath 30 are inserted into the patient, the rigid shape-retaining member 38 retains the corresponding portion of the insertion tube 32 in the selected shape. The sheath's compliant tube 40, however, allows for articulation of the insertion tube's distal end 44 for proper placement of the distal end. Accordingly, a doctor guiding the sheathed insertion tube 32 can steer and control the position of the insertion tube's distal end 44 by twisting the endoscope at the headpiece 48 and the sheath's body 36, thereby twisting the shape-retaining member 38. Once the insertion tube 32 is inserted into the patient to the selected position, the shape-retaining member 38 helps prevent the insertion tube 32 from moving out of position.

The doctor also steers and controls the insertion tube's distal end 44 by manipulating the endoscope's control wheels 72, which articulate the insertion tube's distal end. The compliant tube 40 can bend relatively freely to conform to the shape of the distal end 44 of the insertion tube 32 as it is articulated. The compliant tube 40 is a thin-walled elastomeric tube that allows for articulation of the insertion tube's distal end portion without substantially changing the bending characteristics of the distal end portion. The control wheels 72, consequently, can fully control the orientation of the insertion tube's distal end 44 and the alignment of the viewing window 68.

Particular embodiments of the sheath 30 can have many advantages in the medical, therapeutic or diagnostic fields. A primary advantage is that the endoscope 34 having a flexible insertion tube 32 is more versatile when used in connection with the sheath 30 that changes the bending characteristics of at least a portion of the insertion tube. An operation that is preferably performed with an endoscope 34 having a rigid insertion tube 32 can now be performed with an endoscope having a flexible insertion tube by using that endoscope 34 in combination with the sheath 30 that provides the bending characteristics of a rigid insertion tube. Instead of a facility owning numerous endoscopes 34, each having different bending characteristics, the facility can use a few flexible endoscopes and carry a variety of inexpensive, sterile sheaths 30 that can alter the flexible endoscopes 34 to give them the necessary bending characteristics.

The sheath 30 can be packaged in a sterile state. As a result, endoscopes 34 with flexible insertion tubes 32 can be used in situations requiring sterility. The sterile sheath 30 is quick to install on an endoscope 34. Consequently, once a procedure is finished, the soiled sheath 30 can be removed from the endoscope 34 and discarded, and a new, sterile sheath can be installed on the endoscope 34 quickly and easily. Sterilizing the endoscope 34 is thus not a cause for delay between patients.

FIGS. 5 and 6 illustrate an endoscopic sheath 130 according to another embodiment of the present invention. This embodiment of the sheath 130 includes a body 136, a shape-retaining member defined by a shapeable member 139 connected to the body 136, and a compliant tube 140 connected to the shapeable member 139. The body 136 is essentially the same as that described above, and can have a proximal opening 142, a distal opening 146 and a working port 152.

The shapeable member 139 in the illustrated embodiment is an elongated, flexible tube that is sufficiently bendable to be bent by the user into a selected shape, and it has sufficient stiffness to remain in the selected shape. The stiffness of the shapeable member 139 is such that it retains the corresponding portion of an insertion tube 132 in the selected shape and prevents that portion from bending until the user bends it by hand. The shapeable member 139 has a proximal end 154 sealably attached to a neck 149 of the body 136 defining the distal opening 146. The shapeable member 139 is substantially impermeable so it isolates the corresponding portion of the insertion tube 132 from the external environment. The shapeable member 139 can be made from a tube of a malleable material, such as metal or plastic. The shapeable member 139 can also be fabricated from woven or coiled elements, or otherwise be made from materials or combinations of materials suitable for the above characteristics.

The compliant tube 140 is similar to that defined above, and has a proximal end 162 and a distal end 164. The distal end 164 of the compliant tube 140 projects from the distal end 156 of the shapeable member 139 to receive the distal end 144 of the insertion tube 132 when the insertion tube 132 is fully inserted in the sheath 130. In the illustrated embodiment, the length of the compliant tube 140 extends fully through the inside of the shapeable member 139. The proximal end 162 of the compliant tube 140 and the proximal end of the shapeable members are attached to the neck 149 on the body 136. In an alternate embodiment, the proximal end 162 of the compliant tube 140 is attached to the distal end 156 of the shapeable member 139, so the compliant tube does not extend through the shapeable member. In another alternate embodiment, the compliant tube 140 extends fully over the exterior of the shapeable member 139, thereby containing the shapeable members within the compliant tube.

During use, the sheath 130 is installed onto the endoscope's flexible insertion tube 132 in the manner described above. Once installed, the endoscope 134 combined with the sheath 130 can be used in a similar manner to that described above. In this embodiment, the sheath 130 gives the proximal portion of the flexible insertion tube 132 the bending characteristics of a shapeable insertion tube. The person operating the endoscope 134 can bend the proximal portion of the insertion tube 132 into a selected shape as desired for the particular endoscopic procedure and to optimize the positioning of the insertion tube 132 within a patient's body cavity. The selected shape can be straight or curved, and can have a simple or complex curve. Once the insertion tube 132 is shaped to satisfy the operator, the shapeable member 139 is sufficiently stiff to retain the insertion tube in the selected shape during use.

The portion of the insertion tube 132 lying outside the shapeable member 139 is free to articulate without significant resistance. The operator may consequently manipulate the distal end 144 of the insertion tube 132 to position it in the particular location and orientation desired within the patient's body.

FIGS. 7 and 8 illustrate an endoscopic sheath 230 according to another embodiment of the present invention. The sheath 230 includes a body 236, a compliant tube 240 connected to the body, and a shape-retaining member 241 connected to the body 236 and extending into the proximal portion of the compliant tube. The body 236 is generally shaped the same as those described above, having a neck 249 for receiving a proximal end 262 of the compliant tube 240. The compliant tube 240 overlaps the neck 249 and is attached thereto, such as by glue or a similar adhesive, or it can be attached in another suitable manner.

The shape-retaining member 241 of this embodiment is an elongated element, such as a wire, rod or shaft, oriented axially along a portion of the length of the sheath 230. The shape-retaining member 241 is preferably substantially straight, but can be curved as suitable for particular endoscopic procedures. A proximal end 254 of the shape-retaining member 241 is securely attached to the body 236 and projects from the body 236 in an axial direction along the inside of a portion of the compliant tube 240. The shape-retaining member 241 can also extend along the outside of the compliant tube 240. In the exemplary embodiment, the shape-retaining member 241 is rigid so it is substantially non-bendable under forces typically experienced in endoscopic procedures. The shape-retaining member 241 can be manufactured from any rigid material suitable for the purpose, such as steel, aluminum or plastic. In an alternate embodiment, the shape-retaining member 241 can also be shapeable, such as a malleable rod or flexible cable, that can be bent to a selected position by a user and will remain in that selected position until it is re-shaped by the user.

During use, the sheath 230 is installed on the flexible insertion tube 232 as described above. Once installed, the sheath 230 gives the proximal portion of the flexible insertion tube 232 the bending characteristics of a rigid or semi-rigid insertion tube. The portion of the insertion tube 232 lying within the compliant tube 240 beyond the distal end 256 of the shape-retaining member 241 is freely articulatable without significant resistance. The operator may consequently manipulate the distal end 244 of the insertion tube to position it in the desired location and orientation.

Figure 9:
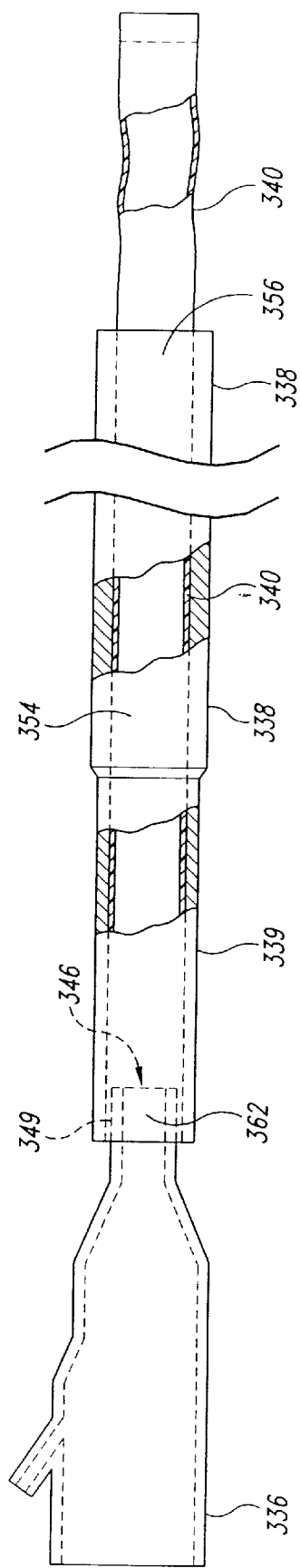
FIG. 9 is a two-part, partially cut-away, side elevation view of a partially rigid, partially shapeable, and partially compliant sheath according to another alternate embodiment of the present invention.
Figure 10:
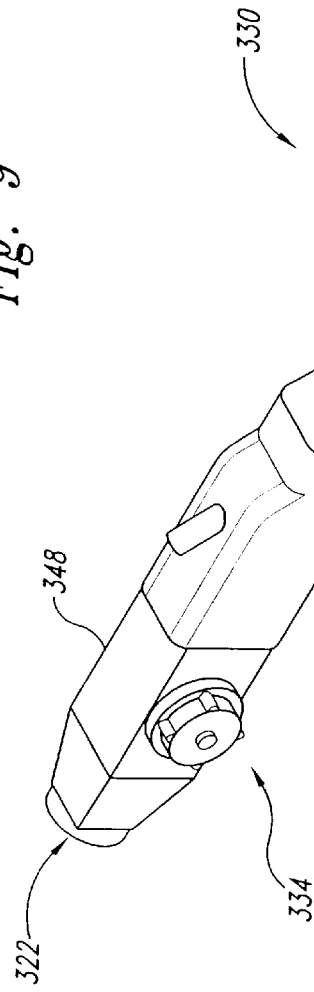
FIG. 10 is a reduced isometric view of the sheath of FIG. 9 installed on a flexible insertion tube of an endoscope.

FIGS. 9 and 10 show another endoscopic sheath 330 according to still another embodiment of the present invention. The sheath 330 includes a body 336, a shapeable member 339 connected to the body 336, a rigid member 338 connected to the shapeable member 339, and a compliant tube 340 projecting from the distal end 356 of the rigid member 338. The compliant tube 340 extends along the inside of the entire length of the rigid member 338 and the shapeable member 339, and it attaches to a neck 349 on the body 336. The compliant tube 340 could also extend along the outside of the rigid member 338, the shapeable member 339, or both. In an alternate embodiment, the compliant tube 340 can be attached to the distal end 356 of the rigid member 338.

The rigid member 338 can be tubular, as shown in FIGS. 9 and 10, or a splint-like structure, such as a rigid rod or shaft oriented axially along a portion of the sheath. The rigid member 338 can be straight or manufactured with a preselected curve to be suitable for one or more particular endoscopic procedures. The shapeable member 339 is sufficiently flexible to be bent by a user, and sufficiently stiff to retain a selected shape and to retain the corresponding portion of the insertion tube 332 (FIG. 10) in the selected shape.

In operation, an endoscope 334 having a flexible insertion tube 332 takes on the bending characteristics of a composite endoscope, such as a laparoscope, wherein the proximal portion is shapeable, the central portion is rigid, and the distal portion is compliant and articulatable. The shapeable member 339 can be bent by the user to independently align the rigid member 338 with respect to both the sheath's body 336 and distal end 344 of the insertion tube 332. This added degree of freedom can allow the headpiece 348 of the endoscope 334 to be fixedly mounted to a table or other structure outside the patient while the distal portion of the insertion tube 332 is manipulated inside the patient. This arrangement helps provide a stable eyepiece 322 for the operator, which allows for better viewing. The portion of the insertion tube 332 within the compliant tube 340 beyond the distal end 356 of the rigid member 338 is free to move without significant resistance. The operator may consequently manipulate the distal end 344 of the insertion tube to position it in the desired location and orientation.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A sheath adapted for use with an endoscope having a flexible insertion tube, the sheath comprising:
    an elongated, compliant tube having an interior area adapted to be occupied by a first portion of the flexible insertion tube and adapted to isolate the first portion of the flexible insertion tube from an external environment; and
    an elongated shape-retaining tube attached to and coaxially aligned along a portion of the compliant tube and adapted to extend axially along a region adapted to be occupied by a second portion of the flexible insertion tube when the first portion of the flexible insertion tube is positioned in the interior area of the compliant tube, the shape-retaining member having a stiffness sufficient to retain the region in a selected shape.

2. The sheath of claim 1, wherein the shape-retaining member is rigid.

3. The sheath of claim 1, wherein the shape-retaining tube is bendable.

4. The sheath of claim 1, wherein the shape-retaining tube is at least partially inside the compliant tube.

5. The sheath of claim 1, wherein the compliant tube is coaxially aligned with and extends along at least the entire length of the shape-retaining tube.

6. The sheath of claim 5, wherein the shape-retaining tube is inside the compliant tube.

7. The sheath of claim 1, wherein the compliant tube has a proximal end and the shape-retaining tube has a distal end attached to the proximal end of the compliant tube.

8. The sheath of claim 7, wherein the shape-retaining tube is rigid, and further comprising a shapeable member having a distal end and a bore, the shapeable member being bendable to a selected shape and being sufficiently rigid to remain in the selected shape, the bore being adapted to be occupied by a third portion of the flexible insertion tube, and the shape-retaining tube being attached at a proximal end to the distal end of the shapeable member.

9. The sheath of claim 1, wherein the shape-retaining tube includes a rigid shaft.

10. The sheath of claim 9, wherein the rigid shaft is at least partially internal to the compliant tube.

11. A sheath adapted for use with an endoscope having a flexible insertion tube, the sheath comprising:
    an elongated, compliant tube having an interior area adapted to be occupied by a first portion of the flexible insertion tube and adapted to isolate the first portion of the flexible insertion tube from an external environment; and
    an elongated, shapeable tube attached to and coaxially aligned along a portion of the compliant tube and adapted to extend axially along a region adapted to be occupied by a second portion of the flexible insertion tube when the first portion of the flexible insertion tube is positioned in the interior area of the compliant tube, the shapeable member being bendable to a selected position and having a stiffness sufficient to retain the region in the selected position.

12. The sheath of claim 11, wherein the shapeable tube is at least partially inside the compliant tube.

13. The sheath of claim 11, wherein the compliant tube extends along the entire length of the shapeable tube.

14. The sheath of claim 11, wherein the compliant tube is adapted to be occupied by a portion of the flexible insertion tube having an outer diameter slightly smaller than an inner diameter of the interior area.

15. A sheath adapted for use with an endoscope having a flexible insertion tube, the sheath comprising:
    an elongated, compliant tube having an internal area adapted to be occupied by at least a first portion of the flexible insertion tube and adapted to isolate the first portion of the flexible insertion tube from an external environment; and
    an elongated, rigid tube coupled to and coaxially aligned along a portion of the compliant tube and adapted to extend axially along a region adapted to be occupied by a second portion of the flexible insertion tube when the first portion of the flexible insertion tube is positioned in the internal area of the compliant tube.

16. The sheath of claim 15, wherein the rigid tube is at least partially inside the compliant tube.

17. The sheath of claim 15, wherein the rigid tube has a distal end attached to a proximal end of the compliant tube.

18. The sheath of claim 15, further including:
    an elongated, shapeable member attached to the rigid tube and positioned to extend axially along a second region adapted to be occupied by a third portion of the flexible insertion tube when the first portion of the flexible insertion tube is positioned in the internal area of the compliant tube, the shapeable member being bendable and having a stiffness sufficient to remain in the selected position.

19. A device for performing intrabody diagnosis, therapy or surgery, the device comprising:

an endoscope having a flexible insertion tube;

an elongated, compliant tube having an interior area configured to receive at least a first portion of the flexible insertion tube and isolate at least the first portion of the flexible insertion tube from an external environment; and an elongated shape-retaining tube attached to and coaxially aligned along a portion of the compliant tube and extending axially along a second portion of the flexible insertion tube when the first portion of the flexible insertion tube is positioned in the interior area of the compliant tube, the shape-retaining tube having a stiffness sufficient to retain the second portion of the flexible insertion tube in a selected shape.

20. The device of claim 19 wherein the shape-retaining tube is rigid.

21. The device of claim 19 wherein the shape-retaining tube is bendable to a selected shape and sufficiently stiff to remain in the selected shape and to retain the second portion of the flexible insertion tube in the selected shape.

22. An endoscope assembly, comprising an endoscope having a flexible insertion tube with a first bending characteristic, the insertion tube having a stiffness, and a sheath positionable to cover at least a first portion of the insertion tube, the sheath including a flexible tube portion and a shape-retaining tube portion attached to and at least partially coaxially aligned with the flexible tube portion, the shape-retaining tube portion being substantially more stiff than the stiffness of the first portion of the insertion tube to provide a second bending characteristic different from the first bending characteristic.

23. The endoscope assembly of claim 22, wherein the flexible tube portion of the sheath is less stiff than the insertion tube.

24. A method for affecting the bending characteristics of a flexible endoscopic insertion tube having a first bending characteristic, the method comprising inserting the flexible insertion tube into a sleeve until a first portion of the flexible insertion tube is within a compliant tube having a second bending characteristic and that extends along a portion of the sleeve and a second portion of the flexible insertion tube that has a third bending characteristic different from the first bending characteristic of the insertion tube and that aligns with a shape-retaining tube connected to and coaxially aligned with a portion of the compliant tube and that has a sufficient stiffness to remain in a selected shape and to retain the second portion of the insertion tube in the selected shape.

25. The method of claim 24, further comprising articulating the first portion of the insertion tube when it is within the compliant tube when the second portion of the insertion tube is in the shape-retaining tube and in the selected position.

26. The method of claim 25, further comprising removing the insertion tube from the sheath.

* * * * *